(12) United States Patent
Chertorizhsky et al.

(10) Patent No.: US 11,365,216 B2
(45) Date of Patent: Jun. 21, 2022

(54) ANTIVIRAL IMMUNOTROPIC AGENT FOR THE TREATMENT OF ACUTE RESPIRATORY VIRAL INFECTIONS

(71) Applicant: PVP LABS PTE. LTD., Singapore (SG)

(72) Inventors: Evgeny Alexandrovich Chertorizhsky, Belkino Village (RU); Mikhail Vladimirovich Ovchinnikov, Moscow (RU); Aleksey Viktorovich Kleimenov, Zhukov (RU)

(73) Assignee: PVP Labs Pte. Ltd., Singapore (SG)

( * ) Notice: Subject to any disclaimer, the term of this patent is extended or adjusted under 35 U.S.C. 154(b) by 144 days.

(21) Appl. No.: 16/221,475

(22) Filed: Dec. 15, 2018

(65) Prior Publication Data

US 2019/0322701 A1    Oct. 24, 2019

(30) Foreign Application Priority Data

Apr. 18, 2018   (RU) ................... 2018114273

(51) Int. Cl.
```
C07K 7/06      (2006.01)
A61P 31/16     (2006.01)
A61K 9/00      (2006.01)
```
(52) U.S. Cl.
CPC .............. *C07K 7/06* (2013.01); *A61K 9/0043* (2013.01); *A61P 31/16* (2018.01)

(58) Field of Classification Search
CPC .......... C07K 7/06; A61P 31/16; A61K 9/0043
See application file for complete search history.

(56) References Cited

U.S. PATENT DOCUMENTS

| | | | |
|---|---|---|---|
| 2010/0113347 A1 | 5/2010 | Nesteruk et al. | |
| 2013/0034572 A1 | 2/2013 | Stanimirovic et al. | |
| 2013/0245100 A1 | 9/2013 | Desmecht et al. | |
| 2015/0152149 A1 | 6/2015 | Zheng et al. | |

FOREIGN PATENT DOCUMENTS

| | | |
|---|---|---|
| RU | 2436588 | 12/2011 |
| RU | 2521199 | 6/2014 |
| RU | 2639559 | 12/2017 |

OTHER PUBLICATIONS

Tian et al, Novel effect of methionine enkephalin against influenza A virus infection through inhibiting TLR7-MyD88-TRAF6-NF-κB p65 signaling pathway, International Immunopharmacology, 2018, 55, pp. 38-48.*
Pencheva et al, Dalargin and [Cys-(O2NH2)]2 Analogues of Enkephalins and their Selectivity for mu Opioid Receptors, Gen. Pharmac., 1995, 26, pp. 799-808.*
Machine translation of RU 2436588 C1, pp. 1-6, accessed May 12, 2020.*
Coussons-Read et al, Morphine Reduces Pulmonary Inflammation in Response to Influenza Infection, Life Sciences, 1999, 65, pp. 1141-1152.*
Tahamtan et al, Opioids and Viral Infections: A Double-Edged Sword, Frontiers in Microbiology, 2016, 7, pp. 1-14.*
Pacheco et al, The mu-opioid receptor agonist morphine, but not agonists at delta- or kappa-opioid receptors, induces peripheral antinociception mediated by cannabinoid receptors, British Journal of Pharmacology, 2008, 154, pp. 1143-1149.*
Top 40 antiviral drugs for influenza, from http://vsebolezni.com/treatment/grippa_tabletki, accessed Aug. 24, 2020, pp. 1-21.*
Newton et al, The host immune response in respiratory virus infection: balancing virus clearance and immunopathology, Semin Immunopathol, 2016, 38, pp. 471-482.*
Pathan et al, Basic opioid pharmacology: an update, British Journal of Pain, 2012, 6, pp. 11-16.*
Nelson et al, Involvement of Central m- but Not d- or k-Opioid Receptors in Immunomodulation, Brain, Behavior, and Immunity, 2000, 14, pp. 170-184.*
Chen et al, Methadone enhances human influenza A virus replication, Addiction Biology, 2015, 22, pp. 257-271.*
Yang et al, The signal pathways and treatment of cytokine storm in COVID-19, Signal Transduction and Targeted Therapy, 2021, 6, pp. 1-20.*
Tomassini et al, Mu and delta receptors mediate morphine effects on phagocytosis by murine peritoneal macrophages, Journal of Neuroimmunology, 2003, 136, pp. 9-16.*
Yarygin, K. N. et al., 'Effect of the hexapeptide dalargin on ornithine decarboxylase activity in the duodenal mucosa of rats in experimental duodenal ulcer', Bulletin of Experimental Biology and Medicine, Mar. 1987, vol. 103, No. 3, pp. 356-358.
Chang AY., et al., Investigating the role of MRGPRC11 and capsaicin-sensitive afferent nerves in the anti-influenza effects expected by SLIGRL-amide in murine airways. Respir Res. May 23, 2016; 17(1); 62. doi 10.1186/s12931-016-0378-8.

* cited by examiner

*Primary Examiner* — Li N Komatsu
(74) *Attorney, Agent, or Firm* — Aleksandr Smushkovich

(57) ABSTRACT

The proposed methods of treatment pertain to medicine, in particular pharmacology, and concerns the application of a nasal medicinal composition containing hexapeptide tyrosyl-D-alanyl-glycyl-phenylalanyl-leucyl-arginine or its pharmaceutically acceptable salt for the treatment of acute respiratory viral infections (ARVIs), in particular those caused by the influenza virus.

12 Claims, 5 Drawing Sheets

Table 1

| Treatment | Inhibition of Virus Reproduction | |
|---|---|---|
| | MIC50, μg/mL | Activity at 10 μg/mL (viable cell ratio in %) |
| ARBIDOL | 6.0 | 100 |
| Dalargin | 0.8 | 100 |

Table 2

| Group | Survival ratio | Mortality % | Average lifetime |
|---|---|---|---|
| Dalargin (IM, 2 mg/kg/day, n = 10) | 9/10 | 10 | 14.0 |
| Dalargin (intranasally, 2 mg/kg/day, n = 10) | 8/10 | 20 | 12.5 |
| ARBIDOL (orally, 60 mg/kg/day, n = 10) | 7/10 | 30 | 11.2 |
| Control (placebo, n=10) | 2/10 | 80 | 8.5 |

FIG. 4

Table 3

| Dosage regimen | Dalargin (dose, μg/ml) | CPE detection rate | CPE suppression (Ki, %) |
|---|---|---|---|
| 24 hours before challenge | 100.0 | 1/10 | 90.0 |
| | 20.0 | 4/10 | 60.0 |
| | 10.0 | 6/10 | 40.0 |
| 2 hours after challenge | 100.0 | 2/10 | 80.0 |
| | 20.0 | 5/10 | 50.0 |
| | 10.0 | 8/10 | 20.0 |
| Control (no treatment) | - | 10/10 | - |
| Medium control | - | 0/10 | - |

FIG. 5

Table 4

| Neutrophils | | |
|---|---|---|
| Group | Phagocytic index | Phagocyte number |
| Control (n = 10), | 19.1 ± 0.45 | 2.25 ± 0.10 |
| Dalargin (IM, 0.2 mg/kg, n = 10) | 32.43 ± 0.56* | 3.01 ± 0.13* |
| Dalargin (nasally, 0.2 mg/kg, n = 10) | 31.87 ± 0.43* | 2.93 ± 0.15* |
| Macrophages | | |
| Group | Phagocytic index | Phagocytic activity (%) |
| Control (n = 10) | 55.2 ± 4.6 | 10.3 ± 0.7 |
| Dalargin (IM, 0.2 mg/kg, n = 10) | 67.7 ± 6.1* | 19.8 ± 1.2* |
| Dalargin (nasally, 0.2 mg/kg, n = 10) | 63.9 ± 5.7* | 19.1 ± 1.1* |

*Comment:* * = significance level $p < 0.05$ (relative to controls)

FIG. 6

ANTIVIRAL IMMUNOTROPIC AGENT FOR THE TREATMENT OF ACUTE RESPIRATORY VIRAL INFECTIONS

CROSS-REFERENCES TO RELATED APPLICATIONS

This application claims priority under 35 U.S.C. 119 (a) through (d), under the Paris Convention, from a Russian Federation patent application RU2018114273 filed 18 Apr. 2018, now Patent of Russian Federation RU2672888, hereby entirely incorporated by reference.

FIELD OF THE INVENTION

The invention pertains to medicine, in particular pharmacology, and concerns the application of a nasal medicinal composition containing the hexapeptide tyrosyl-D-alanyl-glycyl-phenylalanyl-leucyl-arginine or its pharmaceutically acceptable salt for the treatment of acute respiratory viral infections (ARVIs), in particular those caused by the influenza virus.

BACKGROUND OF THE INVENTION

Acute respiratory viral infections (ARVI) are currently the most common type of infections, accounting for over 90% of the total (see Reference [1] below). According to the World Health Organization, over 40 million of new cases are reported yearly. The social burden of ARVIs is mostly characterised by high indirect costs, such as costs for the period of workplace absence, economic losses due to reduced labour productivity, and costs of workplace absence of family members taking care of the patients (economic losses in the USA due to temporary disability only are evaluated at 232 million dollars) [2].

This problem is also extremely relevant for Russia, as according to official figures, 27.3 to 41.2 million cases of respiratory tract infections are reported in the Russian Federation annually. This disease, with a high specific weight in the overall morbidity structure, accounts for almost 40% of days of disability [3].

Over 200 viruses causing flu-like diseases are currently known. Analysis of results of numerous studies of the structure of causes of ARVIs, which were performed in different countries by different research teams, demonstrates that the most common pathogens include rhinoviruses, influenza viruses, parainfluenza viruses, respiratory syncytial virus (RSV), coronaviruses, metapneumoviruses, bocaviruses and adenoviruses [4].

Influenza viruses belong to the group of orthomyxoviruses and have a spherical shape. The internal part of the virus consists of an isopolymerase complex (PA, PB1, PB2), a ribonucleoprotein and a matrix protein. On the outside, the virus is covered with an envelope featuring two types of surface antigens: haemagglutinin (HA) and neuraminidase (NA). These structures enable the virus to attach to the host cell and penetrate it. Surface antigens exhibit variability, which gives rise to new strains of the influenza virus. The greatest variability is exhibited by influenza A viruses, which are capable of causing, within a short time, nationwide epidemics or continent-wide pandemics of influenza. According to the US Center for Disease Control (CDC), seasonal flu epidemics cause 200 thousand hospitalisations per year, while the mortality is 1.4-1.67 per 100 thousand population [5]. A flu pandemic that began in 2009 was caused by an influenza A virus (H1N1) with a pandemic potential. This virus arrived to Russia later, and the greatest number of patients was reported in 2010-2011 and 2015 [6]. Sampling pharmacoepidemiological investigations carried out in 1 462 patients demonstrated, that people from the age bracket of 18-49 years accounted for 84.7% patients [7].

Therefore, prevention of spread of this group of diseases is an important goal for any country. Accordingly, several methods for the treatment and prevention of this group of diseases are available.

Specifically, mass vaccination of the population is the main prophylactic measure intended for preventing epidemics. Vaccines are developed yearly based on epidemiological data on the virus strains circulating within a particular territory. However, the antigenic drift of the influenza virus can occur after the vaccine for the current year has been developed. In recent years, ARVIs caused by several different pathogens have become a common occurrence. According to some estimates, such cases affect 70% patients. A patient may simultaneously shed several viruses, or a virus in combination with bacteria, or other associations. There have been reports indicating that an infection can be caused by one virus, with another virus becoming involved during the progression of the infection, which may aggravate the clinical course of the disease. Such mixed infections often aggravate the condition of the patient, prolong the disease, can exacerbate pre-existing chronic conditions or contribute to secondary complications [8].

Additionally, the treatment of respiratory viral diseases involves antiviral drugs, including peptides with an antiviral effect. For instance, antimicrobial peptides (AMPs) are molecules of the host's own immune defence, which are probably produced by all multicellular plants and animals. They are the first line of congenital immunity, which rapidly eliminates invasive pathogens during the early stages of infection and can cause a systemic adaptive immune response. Most AMPs are amphipathic and cationic molecules capable of binding to microbial membranes, which usually carry a negative charge. Hundreds of AMPs have been identified and classified by their structural features and/or amino acid composition. Two AMP families in vertebrates, cathelicidins and defensins, are small molecules that are mostly produced by leukocytes and epithelial cells.

A composition containing this peptide class is known in the state of the art, where the peptide can suppress various respiratory viral infections. Thanks to a functional domain capable of binding to the surface glycoprotein of a respiratory virus, the peptide can bind to the surface glycoprotein of the virus and reach the inside of endosomes by endocytosis. As the peptide is rich in basic amino acids, it can prevent pH decline in late endosomes, thereby blocking the fusion of viral and endosomal membranes and subsequent degradation of the virus with the release of viral RNA. Therefore, the peptide demonstrates a strong ability to block infections caused by respiratory viruses, such as various subtypes of influenza viruses and coronaviruses; it can be used for blocking target cell infections with respiratory viruses and for preventing or treating viral respiratory infections (patent RU 2639559, 21 Dec. 2017).

However, as mentioned previously, the use of such products is hampered by variability of the genetic material of viruses; consequently, their effect is limited to a specific pathogen responsive to this type of treatment.

Treatment with combination products is also used. For example, the use of combination products with an antipyretic, analgesic, anti-oedematous and angioprotective effect for symptomatic treatment of ARVIs in everyday clinical practice can be considered advisable. The use of combination symptomatic drugs is associated with a reduced incidence of adverse events relative to a set of single-component drugs, and it is more reasonable economically [9].

However, the use of this type of drugs neglects the importance of retaining the nasal respiratory function and factors of local specific and non-specific immunity in patients with ARVIs.

Meanwhile, causes of ARVI include changes in the function of nasal respiration, which is associated with the operation of mechanisms, by which pathogens are removed from inhaled air. This function depends on the production of nonspecific and specific immune protection factors by nasal mucosa and on mucociliary clearance.

Preventative and therapeutic effect of such products is directly related to their ability to remove aggressive organic and inorganic factors of inhaled air from the nasal cavity and normalise non-specific and specific immunity and mucociliary clearance.

The use of products activating the non-specific resistance of the body is a promising area of such prevention. Inducers of endogenous interferons, such as TILORON, ARBIDOL and CYCLOFERON, are widely used in the Russian clinical practice for this purpose.

The dipeptide α-glutamyl-tryptophan in the form of sodium salt is known from the literature (Russian Federation patent 2107691, 1998). This peptide is used as an immunomodulator affecting cell-mediated and humoral immune response and non-specific resistance of the body. It stimulates regeneration processes if they are suppressed, and improves cellular metabolism. It also promotes differentiation of lymphoid cells and can stimulate the colony-forming activity of bone marrow cells, induces the expression of differentiation receptors on lymphocytes, normalises the number of T helper cells and T suppressor cells and their ratio in patients with a variety of immunodeficiency conditions.

This peptide was used in a composition for nasal administration, which was applied for the prevention and/or treatment of upper respiratory tract diseases, in particular, acute respiratory viral infections (ARVI), including influenza. The composition contains active ingredients and excipients; active substances include marine salt and α-glutamyl-tryptophan at the following ratio (weight %):

marine salt: 95.00-98.00;

α-glutamyl-tryptophan: 2.00-5.00 (Patent RU2540496, issued 10 Feb. 2015, which is considered the most relevant related art, herein also called 'prototype').

This nasal medicinal product contains ingredients of seawater and allows for active lavage of the nasal cavity, helping remove the mucus, reduce infected discharge and swelling of the nasal mucosa, soften and remove crusts. The product normalises the protective function of ciliary epithelium of the nasal mucosa and improves nasal respiration.

However, the use of marine salt as an additional ingredient does not exactly enhance the activity of the dipeptide; instead, this degrades its stability and activity. Owing to this, despite the fact that the patent specification mentions the general known immunomodulating property of the peptide, it does not cover direct results of investigations or efficacy comparisons with the antiviral products currently in use, making it impossible to evaluate the antiviral mechanism of action of the product, its antiviral efficacy or selectivity.

These drawbacks necessitate the development of new peptide-based products with a pronounced antiviral effect, which trigger physiological mechanisms inhibiting the development of ARVIs.

In particular, hexapeptide tyrosyl-D-alanyl-glycyl-phenylalanyl-leucyl-arginine (designated as Dalargin) is known in the state of the art.

Dalargin exhibits a non-specific affinity to μ (mu), δ (delta) and κ (kappa) opioid receptors, which explains the wide spectrum of its biological activity: analgesic [9] and antioxidant [10] properties. It is registered in Russia as a product for reducing the acidity of gastric juice and exocrine secretory activity of the pancreas (State Registry of Medicinal Products database: <https://grls.rosminzdrav.ru>). Additionally, the substance is known to exhibit a hypotensive and positive chronotropic effect [11].

Tens of patents demonstrating various effects of Dalargin have been registered as of now. To wit, patent RU 2196603 discloses the use of Dalargin for the treatment of burns as part of infusion therapy. Patents UA 6829LJ, UA 6823U and UA 6826U disclose the use of Dalargin for the treatment of acute experimental pancreatitis. The use of Dalargin as an anti-stress agent was covered in patents UA 67632, UA 67630 and UA 67629 in experimental models of chronic pancreatitis, acute adnexitis and peritonitis respectively. The anti-stress activity of Dalargin was demonstrated in patent UA 67626 in a model of experimental chronic stress.

Patent RU 2180598 discloses the use of Dalargin for the treatment of toxic hepatitis in patients with chronic drug addiction. Publication MD1413F discloses the use of Dalargin for the treatment of the oral mucosa and lichen planus, and publication MD1296F presents data on the therapy of lichen planus with Dalargin. Application RU 2008131509 presents a pharmaceutical composition for the treatment of demyelinating diseases, which includes Dalargin. Patent RU 2218896 discloses the use of Dalargin for the treatment of bullous keratopathy. Publications MD1963F and MD1610F cover the use of Dalargin in cases of chronic recurrent oral ulceration, and patent RU 2230549 covers its use for the treatment of allergic dermatosis.

Additionally, the efficacy of Dalargin in the treatment of several viral diseases was demonstrated in patents RU 2261722 (treatment of a latent form of genital herpes in a woman with the foetal loss syndrome) and RU 2167671 (treatment of tick-borne encephalitis). However, these works do not cover the treatment of ARVIs; they are related to the treatment of other diseases. Additionally, they give no indication of a direct antiviral effect of the hexapeptide in question.

Moreover, despite the fact that patent RU 2241488 describes the use of Dalargin as solution for injections, and application RU 2010152024 describes the application of Dalargin as spray for intranasal pharmaceutical composition, Dalargin in these works is intended for the treatment of gastroenterological diseases.

Interferon-α (IFN-α) secretion was previously demonstrated to increase at 24 and 48 hours after subcutaneous administration of leucine-enkephalin at 10 mg/kg [12], but this effect had not been studied for Dalargin before. There is a sufficient number of studies currently available to confirm that Dalargin exhibits an immunomodulating effect [9, 13, 14, 15, 16]. However, the published reports do not cover the full spectrum of immunomodulating properties of Dalargin; in particular, its effect on the production of cytokines, activity of natural killer cells, interferon-inducing activity or effects on phagocytosis are ignored. In effect, these works fail to demonstrate the enhancement of local immunity under the effect of the hexapeptide.

To summarise the above, the materials published till now fail to consider the antiviral activity of Dalargin as such, do not fully disclose its immunomodulating properties and do not cover the feasibility of using this product in ARVI therapy.

OBJECT AND BRIEF SUMMARY OF THE INVENTION

At the same time, the studies carried out by the instant authors demonstrated that the effects of Dalargin, in particular the direct antiviral effect, ability to enhance the factors of local and systemic immunity after local nasal administration, allow to use it as monotherapy or in combination with other medicinal products as a product for the treatment and prevention of ARVIs, including influenza.

The results allowed the authors to develop and propose for application a nasal medicinal composition containing the hexapeptide tyrosyl-D-alanyl-glycyl-phenylalanyl-leucyl-arginine or its pharmaceutically acceptable salt for the treatment of acute respiratory viral infections (ARVIs), in particular those caused by the influenza virus.

In a particular embodiment of the invention, this disease is influenza.

In a particular embodiment of the invention, the pharmaceutically acceptable salt is tyrosyl-D-alanyl-glycyl-phenylalanyl-leucyl-arginine diacetate.

In a particular embodiment, the nasal composition is prepared in the form of a spray containing, as the active ingredient, the hexapeptide tyrosyl-D-alanyl-glycyl-phenylalanyl-leucyl-arginine or its pharmaceutically acceptable form at the weight percentage of 0.01% to 3% and excipients making up the rest.

In a particular embodiment of the invention, the composition is characterised by containing the hexapeptide tyrosyl-D-alanyl-glycyl-phenylalanyl-leucyl-arginine or its pharmaceutically acceptable salt and excipients at the following ratio of the components in mass %:hexapeptide: 0.01-3%, sodium chloride 7-11%, with water making up the rest.

In a particular embodiment of the invention, the composition is characterised by containing the hexapeptide tyrosyl-D-alanyl-glycyl-phenylalanyl-leucyl-arginine or its pharmaceutically acceptable salt and excipients at the following ratio of the ingredients in mass %:hexapeptide: 0.01-3%, with water making up the rest.

In a particular embodiment of the invention, the composition is characterised by containing the hexapeptide tyrosyl-D-alanyl-glycyl-phenylalanyl-leucyl-arginine or its pharmaceutically acceptable salt and excipients at the following ratio of the components in mass %:hexapeptide: 0.01-3%, sodium chloride 7-11%, benzalkonium chloride 0.1-0.2%, with water making up the rest.

In a particular embodiment of the invention, the composition is characterised by containing, as excipients, sodium chloride and water at the following ratio of the components in mass %:sodium chloride 9%, water 90%.

In a particular embodiment of the invention, the composition is characterised by containing, as water, water for injections.

In a particular embodiment of the invention, the composition is characterised by containing, as water, purified water.

Technical results of the claimed invention are:

extending the technical toolkit for developing nasal compositions for ARVI treatment;

development of products, the application of which can remove organic and inorganic factors of inhaled air from the nasal cavity and normalise non-specific and specific immunological protection.

development of a peptide-based product capable of exhibiting a direct antiviral effect on ARVI-causing pathogens present in the organism and in the portals of entry.

Therefore, the novelty and essence of this invention consists in the development of a product in which the actual antiviral effect of Dalargin is demonstrated for the main ARVI-causing pathogens: influenza viruses and adenoviruses, and the full disclosure of the immunomodulating activity component of Dalargin in the therapy of these diseases.

BRIEF DESCRIPTION OF THE DRAWINGS

FIG. 4:

Figure 1:
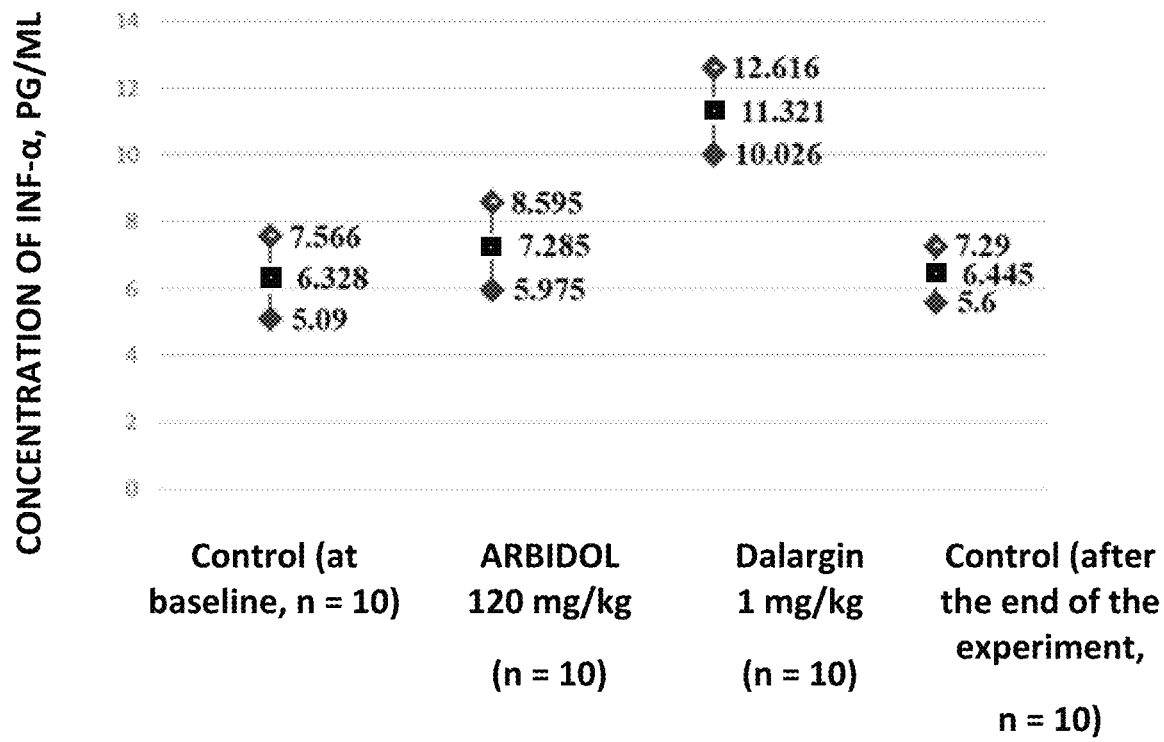
FIG. 1 shows a diagram of concentration of IFN-α in murine blood plasma after the administration of Dalargin, ARBIDOL and placebo.

Table 1 shows minimum inhibitory concentrations (MIC50) and activity of the comparison products relative to the reference strain of the influenza A virus/New Caledonia/20/99 (H1N1) in the MDCK tissue culture.

Table 2 shows antiviral efficacy of the compounds in a model of influenza-induced pneumonia in mice.

FIG. 5—Table 3 shows efficacy of Dalargin versus type 5 adenovirus in a monolayer culture of HeLa cells.

FIG. 6—Table 4 shows the effect of Dalargin on the phagocytic activity of murine neutrophils and macrophages.

DESCRIPTION OF PREFERRED EMBODIMENTS OF THE INVENTION

Examples of implementation of the invention in particular embodiments are presented below.

Example 1. Preparation of Dalargin

A method of production of Dalargin and its pharmaceutically acceptable salt was described previously and is a classical method of peptide synthesis. A description of a method of synthesis of Dalargin is provided below.

Synthesis of H-Phe-Leu-Arg

Dissolve 750 g of Z-Leu-ONSu in 3 L of DMF, add 368 g of Arg to the resulting solution, stir for 24 hours. Evaporate DMF on a rotary evaporator at 41° C. under the vacuum of a rotary vane pump. Dissolve the resulting oil in 15 L of butanol and transfer to a glass desiccator equipped with a stirrer. Add 10 L of distilled water to the desiccator. Stir for 5 minutes until the layers have completely separated (10-24 hours). Decant the water into a clean can. Wash the organic layer 3 more times with 3 L portions of distilled water. Pool the aqueous layer and rinse waters and additionally extract with 4 L of butanol. Evaporate butanol on a rotary evaporator at 43° C. under the vacuum of a diaphragm pump.

Dissolve the resulting oil Z-Leu-Arg in 3 L of ethanol. Transfer the solution to a hydrogenation reactor. Add 50 g of Pd/C suspended in 1.5 L of water. Before hydrogenation, purge the reactor with nitrogen. Pressurise the reactor with hydrogen to 2 kgf/cm$^2$ and start the recirculation pump, maintaining temperature at or below 43° C. Filter the catalyst, wash the reactor with 2 L of distilled water, then wash the catalyst on the filter with the same water. Evaporate the filtrate on a rotary evaporator at 43° C. under the vacuum of a diaphragm pump.

Dissolve the resulting oil H-Leu-Arg in 3 L of DMF and evaporate 1 L on a rotary evaporator under the vacuum of a rotary vane pump. Add solution of 785 g of Z-Phe-ONsu in 2 L of DMF to the resulting solution and stir for 24 hours. Evaporate DMF on a rotary evaporator at 41° C. under the vacuum of a rotary vane pump. Dissolve the resulting oil in 15 L of butanol and transfer to a glass desiccator equipped with a stirrer. Add 10 L of distilled water to the desiccator. Stir for 5 minutes. Wash the organic layer 3 more times with 3 L portions of distilled water. Pool the aqueous layer and rinse waters and additionally extract with 4 L of butanol. Pool butanol portions and evaporate butanol on a rotary evaporator at 43° C. under the vacuum of a diaphragm pump.

Dissolve the resulting oil Z-Phe-Leu-Arg in 3 L of ethanol, to make 6 L of the solution. Transfer the solution to a hydrogenation reactor. Add 50 g of palladium on carbon suspended in 1.5 L of water. Before hydrogenation, purge the reactor with nitrogen. Pressurise the reactor with hydrogen to 2 kgf/cm$^2$ and start the recirculation pump. Recirculation causes heating; maintain the temperature at or below 43° C. After filtering the catalyst, wash the reactor with 2 L of distilled water, then wash the catalyst on the filter with the same water. Evaporate the filtrate on a rotary evaporator at 43° C. under the vacuum of a diaphragm pump. Dissolve the resulting H-Phe-Leu-Arg in 3 L of DMF (approximately 0.6 moles per kg of solution), then use the solution for protein crosslinking.

Synthesis of Boc-Tyr(Boc)-Ala-Gly-ONP

Dissolve 907 g of H-Gly(OBzl)*Tos in 3 L of DMF, adjust pH to 7.2-7.5 with N-methylmorpholine. Add a solution of 773 g of Boc-Ala-ONSu in 2 L DMF in a single portion under cooling on a water bath. T<25° C. Remove the bath and stir at room temperature. TLC control. Evaporate DMF on a rotary evaporator at 41° C. under the vacuum of a rotary vane pump. Dissolve the resulting oil in 15 L of ethyl acetate and transfer to a glass desiccator equipped with a stirrer. Wash the organic layer 3 times with 3 L portions of water. Bring 200 mL of saturated Na2CO3 solution to 3 L with water, wash the organic layer with this solution, then wash 3 more times with 3 L portions of water. Prepare a solution of 6.5 mL 20% sulfuric acid in 3 L of water, wash the organic layer with this solution, then wash 3 more times with 3 L portions of water. At each washing add 0.5 L of ethyl acetate. Evaporate ethyl acetate on a rotary evaporator at 41° C. under the vacuum of a diaphragm pump.

Dissolve the resulting Boc-Ala-Gly(OBzl) in 3.4 kg of trifluoroacetic acid cooled to +5° C. under cooling on an ice bath and vigorous agitation. After complete dissolution, remove the bath and stir for another 1.5 hours at ambient temperature. Evaporate TFA on a rotary evaporator at 41° C. under the vacuum of a diaphragm pump. Then co-evaporate with 0.5 L of benzene three times.

Dissolve the resulting oil H-Ala-Gly(OBzl) in 2.5 L of DMF under cooling on a water bath, adjust pH to 7.2-7.4. Add a solution of 1183 g of Boc2-Tyr-ONSu in 2 L of DMF, T<25° C. Remove the bath and stir at room temperature for 12 hours.

TLC control. Evaporate DMF on a rotary evaporator at 41° C. under the vacuum of a rotary vane pump. Dissolve the resulting oil in 15 L of ethyl acetate and transfer to a glass desiccator equipped with a stirrer. Wash the organic layer 3 times with 3 L portions of water. Bring 200 mL of saturated Na2CO3 solution to 3 L with water, wash the organic layer with this solution, then wash 3 more times with 3 L portions of water. Prepare a solution of 7.5 mL of 20% sulfuric acid in 3 L of water, wash the organic layer with this solution, then wash 3 more times with 3 L portions of water. Evaporate ethyl acetate on a rotary evaporator at 41° C. Dissolve the oil in 2.6 L of hot isopropyl alcohol and portionwise, over approximately one hour, add 7.5 L of hexane, stir until a precipitate is produced. Filter the precipitated Boc2-Tyr-Ala-Gly(OBzl), wash 2 times with 5 L portions of hexane/IPA mixture (4.2/0.8). Dry in ambient air. Yield 1300 g.

Dissolve the resulting Boc2-Tyr-Ala-Gly(OBzl) in 5 L of ethanol, to make 6 L of the solution. Transfer the solution to a hydrogenation reactor. Add 50 g of palladium on carbon suspended in 1.5 L of water. Before hydrogenation, purge the reactor with nitrogen. Pressurise the reactor with hydrogen to 2 kgf/cm$^2$ and start the recirculation pump. Recirculation causes heating; maintain the temperature at or below 43° C. TLC control in 3 hours. Filter the catalyst, evaporate the filtrate on a rotary evaporator at 41° C. under the vacuum of a diaphragm pump. Dissolve in 2 L of DMF, evaporate 1 L on a rotary evaporator at 41° C. under the vacuum of a rotary vane pump. Add 1 L of DMF and 3.5 L of ethyl acetate, then add a solution of 310 g of nitrophenol in 0.5 L of ethyl acetate and 0.3 L of DMF. Cool to –18° C. Prepare a solution of 470 g of DCC in 0.8 L of ethyl acetate and 0.4 L of DMF. Cool to –18° C. After thermal equilibration, mix both solutions and leave them for 24 hours at ambient temperature. Filter the precipitated urea, wash twice with 2 L portions of ethyl acetate. Evaporate the filtrate on a rotary evaporator under the vacuum of a diaphragm pump and then rotary vane pump at 41° C. Crystallize the precipitated oil from hot isopropanol and hexane at the following ratio: take 0.8 L of isopropanol and 0.4 L of hexane per 0.6 mol of Boc2-Tyr-Ala-Gly-ONP, stir until a precipitate is produced. Filter the precipitated Boc2-Tyr-Ala-Gly-ONP, wash 2 times with 5 L portions of hexane/isopropanol mixture (1/2). Yield 1170 g.

Dissolve 530 g of Boc2-Tyr-Ala-Gly-ONP in 1.2 L of DMF and, under cooling on a water bath, add it to the calculated amount of a solution of H-Phe-Leu-Arg (1/1). Stir for 2 hours. Evaporate DMF on a rotary evaporator at 41° C. under the vacuum of a rotary vane pump. Dissolve the oil in 3.2 L of hot isopropanol and portionwise add 4.5 L of hot hexane under stirring. Once the solution cools down to approximately 40-45° C., add 110 g of glacial acetic acid. Stir for 2 hours, obtaining a precipitation. Filter the precipitation, and wash it 2 times with 1.5 L portions of hexane/isopropanol mixture (2/1). Dry in ambient air. Yield 700 g.

Synthesis of Dalargin

Dissolve 100 g of Boc2-Tyr-Ala-Gly-Phe-Leu-Arg in TFA under cooling on an ice bath. Stir for one hour after completely dissolved. Evaporate the TFA on a rotary evaporator at 41° C. under the vacuum of a diaphragm pump. Mix the residue with 1.5 L of diethyl ether, filter, and wash 3 times with ether. Allow to dry under the vacuum of a diaphragm pump at 35° C. for 6 hours. Yield 95 g.

Example 2. Preparation of a Nasal Composition of the Hexapeptide

Preparation of a Dalargin-containing composition in spray form includes: preparation of Dalargin solution, vial filling.

In order to prepare the nasal composition, add 0.01 to 3 g of the hexapeptide (depending on the composition of the solution) to 50 mL of water for injections at 20-25° C. Bring the resulting solution to 100 mL with water for injections. Sterilise the resulting solution by membrane filtration under aseptic conditions by passing it through a 0.22 m filter, fill in polymer or glass vials under an inert gas blanket, close the vials with the finished product.

Additionally, sodium chloride can be added as part of the composition preparation process. To do this, dissolve 7 to 11 g of sodium chloride (depending on the composition of the solution) in 50 mL of water for injections at 20-25° C. under stirring. Then add 0.01 to 3 g of the hexapeptide (depending on the composition of the solution) under stirring. Bring the resulting solution to 100 mL with water for injections. Sterilise the resulting solution by membrane filtration under aseptic conditions by passing it through a 0.22 m filter, fill in polymer or glass vials under an inert gas blanket, close the vials with the finished product.

Additionally, benzalkonium chloride can be added as part of the composition preparation process. To do this, dissolve 7 to 11 g of sodium chloride (depending on the composition of the solution) and 0.1-0.2 g of benzalkonium chloride in 50 mL of purified water for injections at 20-25° C. under stirring. Then add 0.01 to 3 g of the hexapeptide (depending on the composition of the solution) under stirring. Bring the resulting solution to 100 mL with purified water. Sterilise the resulting solution by membrane filtration under aseptic conditions by passing it through a 0.22 m filter, fill in polymer or glass vials under an inert gas blanket, close the vials with the finished product.

This method can be used for producing formulations of the following composition:

| Name | Content, g/mL |
|---|---|
| Hexapeptide (as a physiologically acceptable salt) | 0.01-3 |
| Water for injections | up to 100 mL |
| Hexapeptide (as a physiologically acceptable salt) | 0.01-3 |
| Sodium chloride | 7-11 |
| Water for injections | up to 100 mL |
| Hexapeptide (as a physiologically acceptable salt) | 0.01-3 |
| Sodium chloride | 7-11 |
| benzalkonium chloride | 0.1-0.2 |
| Purified water | up to 100 mL |

Results of experiments confirming the efficacy of Dalargin as an antiviral and immunomodulating product are presented below. The studies provided in these examples were designed and performed in accordance with the effective procedural guidelines pertaining to the preclinical development of antiviral medicinal products, immunomodulating products and interferon inducers [17].

Example 3. In Vitro Investigation of the Antiviral Activity of the Hexapeptide Versus the Reference Strain of the Influenza A/H1N1 Virus A test was performed relative to ARBIDOL using strains of influenza A virus/New Caledonia/20/99 (H1N1) in a model of MDCK tissue culture.

As ARB IDOL exhibited a 100% inhibiting effect (on the reproduction of epidemic virus strains) at a concentration of 10.0 μg/mL, this concentration in water was chosen for comparing the antiviral efficacy of the products under conditions of identical degree of infection with the influenza A virus.

Additionally, the concentrations inhibiting virus reproduction by 50% (MIC50) were calculated for each product.

It can be seen from the data presented in Table 1 (FIG. 4) that both substances exhibit a high antiviral activity relative to strains of the influenza A virus/New Caledonia/20/99 (H1N1), with the hexapeptide having lower MIC values, under extremely low concentrations in solution.

Example 4. Investigation of the Antiviral Efficacy of Dalargin Relative to the Influenza a Virus in a Model of Pneumonia in Mice Mice (n=40, BALB females, mean weight 18-22 g) were challenged intranasally with the influenza A virus/Aichi/2/69 (H3N2) under a mild anaesthesia with ether. The virus dose containing 10 LD50 was determined in advance. To this end, groups of 5-6 mice were challenged with 50 μL of whole virus from the allantoic fluid and a series of its 10-fold dilutions (from $10^{-1}$ to $10^{-6}$). The data suggested that the LD50 corresponded to a 10-3 dilution of the virus. All the animals were then challenged with a 10-fold median lethal dose of the virus in 50 μL.

ARBIDOL was chosen as active control. Four groups of animals (10 animals each) were randomly composed (by randomisation):
control group (saline);
ARBIDOL group;
IM Dalargin group;
intranasal Dalargin group.

Dalargin, ARBIDOL and placebo dosage regimen: 24 h and 1 h before the challenge, then every 24 hours after the challenge for 5 days. Dalargin was administered at a daily dose of 2 mg/kg IM or intranasally. ARBIDOL was administered via a stomach tube (orally).

Dalargin was administered as a pharmaceutical composition diluted to the required concentration as in Example 2, with or without sodium chloride, in order to achieve the recommended volumes for the intramuscular (0.5 mL) or intranasal (0.01 mL) route of administration.

The treated and control animals were monitored daily. The mice were weighed on days 3, 5 and 15 after the challenge.

The chemotherapeutic activity of the compounds in the model of influenza-induced pneumonia in mice was evaluated using two criteria: 1) mean lifetime and 2) weight loss over time (relative to the control group).

The mean lifetime of mice was calculated using the formula MSD=f*(d−1)/n, where f is the number of mice that died at day d; surviving mice are also included in f, and d in this case is 15; n is the number of mice in the group).Σ

The mice were weighed on days 3, 5 and 15 after the challenge. Weight loss or gain was calculated separately for each mouse and expressed in percent. The weight of the animal before the challenge was taken as 100%. The mean weight loss or gain percentage was calculated for all the mice within a group.

In the control group, weight loss was greatest on day 5 post-challenge. In the groups receiving the test drugs, weight reduction was statistically significantly less than in both control groups. The groups receiving Arbidol or Dalargin exhibited no significant differences in weight loss over time relative to each other.

The mean lifetime of mice in the control group was the lowest, at 8.5 days. Treatment with Arbidol or Dalargin increased the mean lifetime of the animals, which grew to 11-14 days. However, the therapy, while allowing to increase the proportion of animals surviving after the challenge (relative to placebo), failed to completely prevent animal mortality (Table 2—FIG. 4).

The data indicate that IM or intranasal administration of Dalargin at 2 mg/kg/day for 5 days reduces the mortality of mice due to influenza-induced pneumonia and reduces weight loss relative to placebo. Dalargin demonstrated greater efficacy relative to Arbidol in terms of the mean lifetime and survival rate. Intramuscular and intranasal administration of Dalargin yielded similar results in terms of the antiviral activity.

Example 5. Experimental Testing of the Antiviral Efficacy of Dalargin Relative to Adenovirus Infection The work was performed using type 5 adenovirus, which was procured in 1998 from the D.I. Ivanovsky Research Institute of Virology and stored in the Specialised Collection of a branch of the 48th Central Research Institute of the Ministry of Defence of Russia—Computing Centre.

A HeLa type culture (cervical carcinoma cells) with a density of 200-250 thousand/mL was used. Semisynthetic growth media based on Hank's solution containing 7.5 and 2% bovine serum respectively were used. A 48-hour monolayer culture of HeLa cells was infected with type 5 adenovirus at a dose of 0.01 TCID50 per cell. The monolayer culture was then incubated at 37±0.5° C. for 96 hours.

The antiviral activity of the product was evaluated by the suppression of the cytopathogenic effect (CPE) of the virus in the HeLa culture after the virus was applied to an established monolayer culture of HeLa cells.

Efficacy criteria of the test drug were: CPE detection rate and inhibitory constant (Ki, %). The inhibitory constant was calculated according to the following formula: Ki=100. (Cc-Ct)/Cc, where Cc and Ct is the infectious titre of the virus in the control sample and test sample respectively.

When Dalargin was administered 24 h before the monolayer culture was challenged with the adenovirus at a dose of 0.01 TCID50 per cell at concentrations of 100, 20 and 10 g/mL, the product almost completely protected the cells from the cytopathogenic effect of the virus. At 10 μg/mL, the protective efficacy of the product was 40.0%. When Dalargin was administered to the maintenance medium 24 h before the challenge, the protective efficacy of the product grew by 10-20% relative to administration of the drug at 2 hours after the challenge.

Therefore, the application of Dalargin suppressed the reproduction of type 5 adenovirus in a monolayer HeLa culture, and the results corroborate the antiviral efficacy of the study drug with respect to the adenovirus infection (Table 3). Examples 3 and 5 herein above prove the specific antiviral properties, herein collectively called a 'direct antiviral effect' discovered by the instant inventors.

Example 6. Evaluation of the Interferon-Inducing Effect of Dalargin in Mice

In all viral infections, interferons (INF) are produced as part of the early cytokine response. They cause ribosomes to produce a number of enzymes that inhibit transcription and translation of the viral genome, which suppresses virus reproduction. Altered cells infected by the virus are eliminated with the aid of NK cells and cytotoxic T cells, whereby the antiviral defences of non-infected cells are activated due to the effect of IFN-α and IFN-β. For this reason, the search for non-toxic inducers of endogenous interferon, as well as pathways for stimulating its production, are of major interest and importance for medical virology [18, 19].

ARBIDOL, an antiviral product with interferon-inducing activity, was chosen as the comparator drug.

The experiments were performed in 40 CBA×C57BI/6/ male mice with a body weight of 20-25 g. The animals were randomised in 4 groups (of 10 animals each): two active groups (receiving Dalargin or ARBIDOL) and two control groups. One control group was intended for determining baseline INF levels (before the start of the experiment), the other group was intended for determining INF levels at 24 hours after the administration of placebo (saline), ensuring the equivalence of conditions.

The animals were housed in cages in a soundproofed room with a natural light-dark cycle at 20-22° C.; feed and water were available ad libitum.

Dalargin was administered at a dose of 1 mg/kg, which is equivalent to a human dose of 5-6 mg. ARBIDOL was administered intragastrically as a suspension premix in 1% starch gel. Statistical analysis was performed using the Bonferroni correction for multiple testing.

IFN-α levels in the blood plasma of mice was measured at 24 hours after the administration of the drugs. Blood for interferon determination was sampled from the heart under Nembutal anaesthesia (60 mg/kg). The blood samples were left at room temperature for 2 hours to induce coagulation, blood plasma was separated by centrifugation, pooled (2 mice per pool), frozen and stored at −20° C. until the tests. IFN levels were determined using commercially available enzyme-linked immunosorbent assay (ELISA) kits manufactured by VeriKine™ (USA). ELISA was performed after a twofold dilution of the pooled serum with the diluents recommended in the manual of the kit manufacturer.

The test samples and diluted standards were applied to the plate in duplicate. In the solid-phase immunoassay employed, the analyte is an antigen (Ag) with two binding sites (epitopes), and the recognizing agent is represented by two types of monoclonal antibodies (Ab) (sandwich ELISA). One type of Ab is immobilised on the solid phase and binds to one epitope of the analyte molecule, which is present in the liquid phase; the second type of Ab is present in a biotin conjugate and binds to the second epitope in the analyte molecule. Horseradish peroxidase conjugated with streptavidine is the indicator component. Tetramethylbenzidine (TMB) was used as the substrate in the detection system. The activity of bound peroxidase was measured on a UNIPLAN™ (Picon) immunoassay analyser at 450 nm.

Control groups exhibited no differences in IFN levels before and after dosing with placebo (saline). Numerical (but insignificant) elevation in IFN-α levels was detected in blood serum samples collected for analysis at 24 hours after dosing with ARBIDOL.

Meanwhile, the Dalargin group demonstrated a significant production of INF-α both relative to the control groups and relative to ARBIDOL ($p<0.001$) (FIG. 1).

Example 7. Evaluation of the Effect of Dalargin on the Functional Activity of Natural Killer (NK) Cells Natural killer cells are large granular lymphocytes with a CD3-CD16+CD56+phenotype, which can recognize and kill target cells without prior sensitisation, which is especially important in the functioning of antitumour immunity and in cases of infestation with intracellular parasites.

When evaluating the effect of Dalargin in vitro on the functional activity of NK cells, these cells were obtained from a suspension of peripheral blood mononuclear cells of healthy donors (n=20).

Functional activity of NK cells was determined on the basis of the cytotoxic reaction (NK can lyse cells of myeloblastoid and lymphoblastoid lines) using the radiometric assay. To perform it, cells of the K-562 myeloblastoid line at a concentration of $10^6$/mL were incubated for one hour at 37° C. with $^3$H-uridine at 3 μCi/mL of the cell suspension on day 2 after subcultivation. After the incubation, the cells were washed off the radiolabel in medium 199 three times.

The cytotoxic reaction was carried out in 200 μL samples in round-bottom 96-well plates. To this end, 100 μL of labelled target cells and 100 μL of mononuclear (effector) cells of the peripheral blood of a donor were mixed at a 1:50 ratio in triplicate for each dilution.

In one case, after the effector cells and target cells were applied to the plates, Dalargin was added at a molar concentration of $5.10^{-8}$ M (≈0.036 μg/mL). The drug was not added to control samples. In order to determine the released label, an equal amount of Triton X-100 was added to the target cells. The plates were then incubated for 24 hours in a CO2 incubator at 37° C., whereupon the contents were transferred to fibreglass filters, washed, dried, placed in vials with a scintillation liquid, and radioactivity was determined using a β-particle counter. cytotoxicity index (CI) was determined using the formula CI=((A–B)/(C–B)). 100%, where A is radioactivity of target cells in the presence of effector cells, B is residual radioactivity after treating the target cells with Triton X-100, C is radioactivity in target cells in the absence of effector cells.

Figure 2:
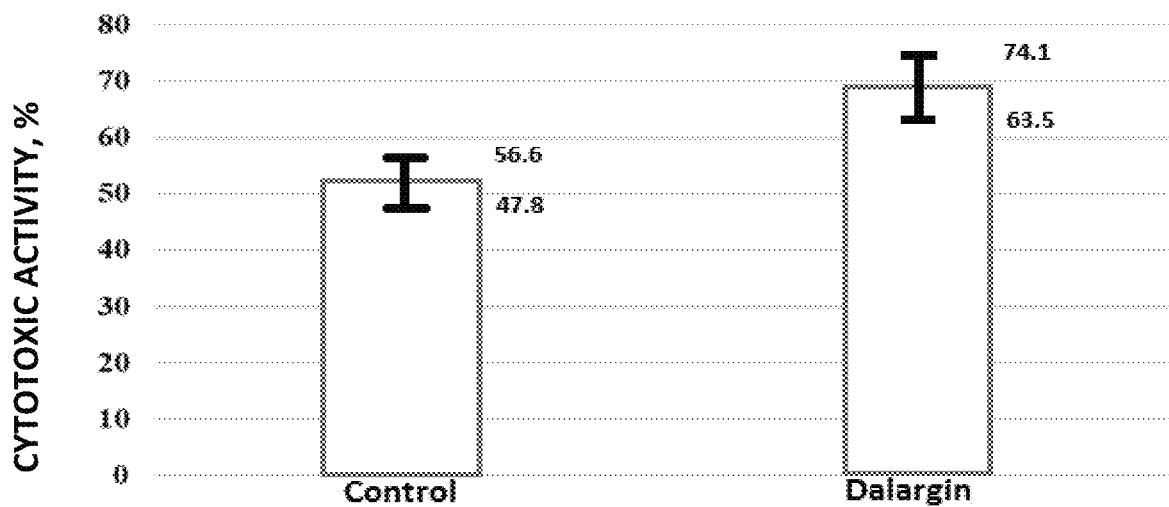
FIG. 2 shows a diagram reflecting an effect of Dalargin on the cytotoxic activity of natural killer cells.

As shown in FIG. 2, results of the test indicate the immunotropic potential of Dalargin with respect to natural killer cells.

Example 8. Investigation of the Effect of Dalargin on Phagocytosis

Dalargin is currently authorised for human use in the single dose range from 1 to 5 mg [20], which, if recalculated for mice, corresponds to z0.2-1 mg/kg. Therefore, the dose used for evaluating the efficacy of the drug in murine phagocytic peritoneal exudate cells was 0.2 mg/kg. Of additional interest was an investigation of possible effect of the route of administration of the drug on functional activity of the phagocytes.

The immunomodulating activity of the drug was evaluated by microscopy. The test was performed in 60 male BALB/c mice with a body weight of 18-22 g. The animals were allocated to 6 equal groups of 10 mice each. Two groups served as controls. The active therapy groups received Dalargin IM or intranasally at a single dose of 0.2 mg/kg. Macrophage and neutrophil extraction procedures were performed on the next day after administering the study drugs.

The mice were given an intraperitoneal injection of 3-4 mL of 10% peptone solution as a chemoattractant to cause neutrophil accumulation, and 2 hours later the mice were euthanised using chloroform 2 hours later. They were subsequently necropsied under aseptic conditions. Liquid from the abdominal cavity was withdrawn using a Pasteur pipette, placed in test tubes and centrifuged for 10 min at 1000 rpm. The precipitate was then resuspended to achieve neutrophil concentrations of 2.5 million/mL.

In order to isolate macrophages, the mice were euthanised on day 3 after the peptone injection. Then 3-4 mL of medium 199 with 10% of foetal bovine serum was administered intraperitoneally, and the liquid was aspirated.

Staph. aureus bacteria (of a protein A-free strain) pre-opsonised with pooled murine serum (10 min. at 37° C.) were added to an equal volume of the phagocytic cell suspension at a 10:1 ratio (i.e. 25 million/mL). A smear was prepared after incubation (Romanovsky-Giemsa staining).

The phagocytic activity of neutrophils was evaluated by the following parameters: phagocytic index and phagocyte number. Functional activity of macrophages was evaluated by microscopy, as well as by their ability to absorb nitroblue tetrazolium (NBT) in the activated state.

The results demonstrated that Dalargin (0.2 mg/kg) was capable of increasing the phagocytic activity (phagocytosis) of peptone-mobilised neutrophils in mice. The route of administration had no effect on efficacy. Dalargin also exhibited a stimulating effect on the phagocytosis of peritoneal exudate macrophages, enhancing their ability to reduce NBT. No differences related to the route of administration were detected (Table 4).

Therefore, Dalargin exhibited a stimulant effect on the phagocytic component of nonspecific immunity.

Example 9. Evaluation of the Effect of Dalargin on the Production of Pro-Inflammatory Cytokines The effect of Dalargin on the synthesis of cytokines IL-1 (interleukin-1), IL-6 (interleukin-6) and TNF-α (tumour necrosis factor α) was evaluated in an in vitro experiment using a peripheral blood mononuclear cell culture of healthy donors (n=20). Stimulation with an enterobacterial polysaccharide was used to induce the production of pro-inflammatory cytokines.

In order to obtain a suspension of mononuclear cells, blood was diluted at a 1:2 ratio with medium 199, applied to a Ficoll-Paque density gradient, d=1.077 g/cm$^3$, and centrifuged at 400 g for 40 min. The white ring produced at the phase interface, which contained mononuclear cells, was carefully withdrawn with a Pasteur pipette and washed twice with medium 199 using 10-minute-long centrifugation (200 g). The precipitate was resuspended in a nutrient medium, counted in a Goryayev counting chamber and adjusted to the required concentration.

Dalargin was added at a molar concentration of $5.10^{-8}$ M (Z0.036 μg/mL) to the test samples with the polysaccharide and mononuclear cell suspension. The drug was not added to control samples.

Cytokine quantitation in blood serum was performed using two-site ELISA.

Figure 3:
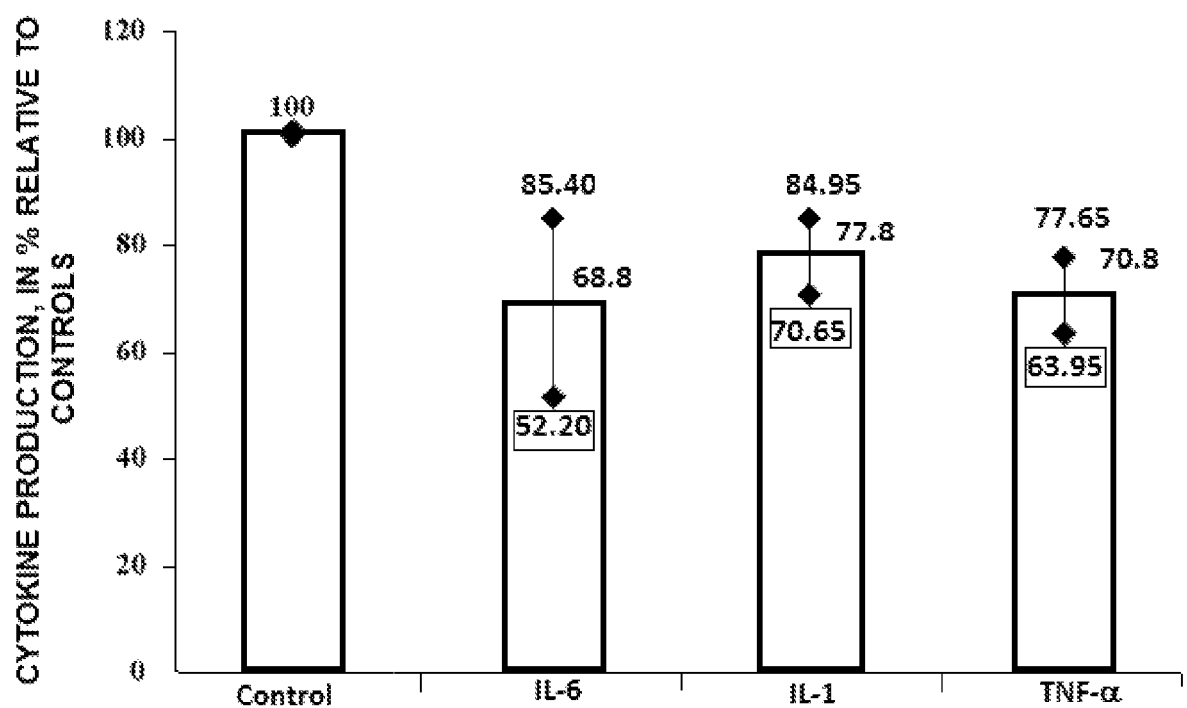
FIG. 3 shows a diagram reflecting suppression of synthesis of pro-inflammatory cytokines under the effect of Dalargin.

The results presented in FIG. 3 demonstrate significant suppression of lipopolysaccharide-induced production of IL-6, IL-1 and TNF-α by Dalargin. The degree of production of the pro-inflammatory cytokines was presented as a ratio relative to their concentration in control samples, which was taken as 100%.

Therefore, it should be noted that the test hexapeptide exhibits antiviral and immunomodulating properties. It regulates the activity of cells of congenital an adaptive immunity. Dalargin enhances the activity of the phagocytic component of immunity (macrophages and neutrophils) and the activity of natural killer cells. The product also stimulates the production of endogenous interferons.

In addition, Dalargin, by suppressing hypersecretion of pro-inflammatory cytokines (IL-1, IL-6 and TNF-α), can reduce intoxication and control other manifestations of the inflammatory cascade.

Therefore, the pharmaceutical composition demonstrated antiviral activity in an experiment in mice receiving Dalargin intranasally at 2 mg/kg/day, which corresponds to a human dose of 10 mg daily.

The volume of solution for a single intranasal administration to humans is 1-2 drops per nostril (for a total of 2-4 drops), corresponding to a volume of 0.1-0.2 mL.

The tests performed justify a conclusion that the human-equivalent concentration of the pharmaceutical composition for intranasal administration is 0.01-30 mg/mL (0.01-3% Dalargin solution).

When administered intranasally, the composition exhibits antiviral and immunomodulating effects comparable to intramuscular administration, which is especially relevant for clinical application.

REFERENCES

[1] Influenza and flu-like infections (including especially dangerous forms of influenza infections). Fundamental and applied aspects of investigation. Bulletin of the Task Committee. Eds.: V. I. Pokrovsky, D. K. Lvov, O. I. Kiselyov, F. I. Yershov. St. Petersburg, Roza mira, 2008.
[2] Sullivan K M, Monto A S, Longini I M. Estimates of the US health impact of influenza. AmIPublicHealth, 1993, 83: 1712-1716.
[3] According to reports of the Federal State Healthcare Institution "Federal Centre for Hygiene and Epidemiology of Rospotrebnadzor of the Russian Federation". Available at: http://www.fcgsen.ru/.
[4] Turner R. Epidemiology, pathogenesis and treatment of the common cold. Annals of allergy,asthma and immunology, 1997, 78: 531-539.
[5] Hayden F, Couch R. Clinical and epidemiological importance of influenza A viruses resistant to amantadine and rimantadine. Reviews in Medical virology, 1992, 2: 89-96.
[6] O. I. Kiselyov, E. G. Deyeva, T. V. Sologub, V. V. Tsvetkova. Recommendations for the Treatment and Prevention of Influenza in Adults. Influenza Research Institute of the Healthcare Ministry of Russia. St. Petersburg, 2014, 4.
[7] E. P. Selkova. Current Problems of Symptomatic and Pathogenetic Treatment of Acute Respiratory Viral Infections. Reference Book of the Polyclinic Phycician, 2013, 01: 9-13.
[8] E. P. Selkova. New Technologies in the Prevention and Treatment of Acute Respiratory Viral Infections. Consiliummedicum. Pediatriya, 2007, 1: 66-68.
[9] N. B. Lazareva, M. V. Zhuravlyova, L. R. Panteleyeva. ARVI: Rational Pharmacotherapy from the Standpoint of Clinical Pharmacology//Meditsinsky Sovet.—2016.—No. 4.
[10] B. V. Balachevsky, A. N. Kurzanov, A. A. Slavinsky. Dalargin-induced Modulation of Functional-Metabolic Activity of Neutrophilic Leukocytes//Uspekhi Sovremennogo Yestestvoznaniya.—2008.—No. 5.
[11] A. N. Zokhirov et al. Effect of Dalargin, a Synthetic Analogue of Opioid Peptides, on the Anti-oxidant Status of Dogs//Vestnik Kurskoy Gosudarstvennoy Selskokhozyaystvennoy Akademii.—2016.—No. 9.
[12] L. N. Maslov et al. Cardiovascular Effects of D-Ala2, Leu5, Arg6-enkephalin (Dalargin) are Associated with the Activation of Peripheral Opioid-Receptors//Eksperimentalnaya i Klinicheskaya Farmakologiya.—2008.—Vol. 71.—No. 2.—p. 21-28.
[13] Gabrilovac, J., Ikic-Sutlic, M., Knezevic, N., &Poljak, L. (1996). Leu-enkephalin enhances interferon secretion in mice. Research in experimental medicine, 196(1), 137-144.
[14] V. Yu. Cherdakov et al. Application of Regulatory Peptides: Timogen, Dalargin, Glycyl-histidyl-lysine and Combinations Thereof, for the Correction of the Neutrophilic Component of Anti-Infection Immunity in Femur Fractures//Kursky Nauchno-Praktichesky Vestnik Chelovek.
[15] M. A. Zemskov et al. Peculiarities of Immunological Disturbances and their Correction in Infections of Different Origin//Vestnik Novykh Meditsinskikh Tekhnologiy.—2011.—Vol. 18. —s. 3.
[16] O. I. Chernyshyova, I. I. Bobyntsev. Biological Effects of the GLY-HIS-LYS Peptide//Mezhdunarodny Zhurnal Prikladnykh i Fundamentalnykh Issledovaniy.—2014.—No. 11-4.—p. 688-692. 23
[17] V. A. Zemskova, S. S. Zemskova, V. I. Domnich, V. I. Shabunina. Mechanisms of Action of Differentiated Immunotherapy of Suppurative-Inflammatory Diseases of Various Origin//Prikladniye Informatsionniye Aspekty Meditsiny.—2009.—Vol. 12.—No. 2.—p. 71-77.
[18] Guidelines on the Clinical Studies of Medicinal Products; Part one. Moscow. Grif i K, 2012.—944 p.
[19] I. E. Makarenko et al. Possible Routes and Volumes of Administration of Medicinal Products to Laboratory Animals//Mezhdunarodny Vestnik Veterinarii.—2013.—No. 3.—p. 78-84.
[20] F. I. Yershov, O. I. Kiselyov. Interferons and their Inductors (from Molecules to Drugs). Moscow, GEOTAR-Meida.—2005.—368 p.
[21] V. P. Kuznetsov. Interferons in the Cytokine Cascade: Historical and Modern Aspects.//Antibiotiki i Khimioterapiya. 1988.—Vol. 43.—X25.—-C.28-40.
[22] Instruction for use of the medicinal product for human use Dalargin-Deko (LP-004596, web portal of the State Registry of Medicinal Products https://grls.rosminzdrav.ru/, accessed 31 Jan. 2018).

We claim:

1. A method of stimulating phagocytosis of neutrophils and macrophages and production of endogenous interferons during treatment of acute respiratory viral diseases (ARVI) in a subject in need thereof, wherein the method comprises intranasally administering a nasal medicinal composition comprising hexapeptide tyrosyl-D-alanyl-glycyl-phenylalanyl-leucyl-arginine or a pharmaceutically acceptable salt thereof.

2. The method according to claim 1, wherein the disease is influenza.

3. The method according to claim 1, wherein the pharmaceutically acceptable salt is tyrosyl-D-alanyl-glycyl-phenylalanyl-leucyl-arginine diacetate.

4. The method according to claim 1, wherein the nasal medicinal composition is in the form of a spray comprising, as the active ingredient, the hexapeptide tyrosyl-D-alanyl-glycyl-phenylalanyl-leucyl-arginine or its pharmaceutically acceptable salt thereof at the weight percentage of 0.01% to 3% and excipients making up the rest.

5. The method according to claim 4, wherein the composition comprises the hexapeptide tyrosyl-D-alanyl-glycyl-phenylalanyl-leucyl-arginine or its pharmaceutically acceptable salt thereof and the excipients at the weight percentage of: 0.01-3% hexapeptide, with water as the excipients making up the rest.

6. The method according to claim 4, wherein the composition comprises the hexapeptide tyrosyl-D-alanyl-glycylphenylalanyl-leucyl-arginine or its pharmaceutically acceptable salt thereof and the excipients at the weight percentage of: 0.01-3% hexapeptide, 7-11% sodium chloride, with water making up the rest.

7. The method according to claim 6, wherein the composition comprises the hexapeptide tyrosyl-D-alanyl-glycyl-phenylalanyl-leucyl-arginine or its pharmaceutically acceptable salt thereof and the excipients at the weight percentage of: 0.01-3% hexapeptide, 7-11% sodium chloride, 0.1-0.2% benzalkonium chloride, with water making up the rest.

8. The method according to claim 1, wherein the composition comprises, as excipients, sodium chloride and water at the weight percentage of: 9% sodium chloride, and 90% water.

9. The method according to claim 5, wherein the composition comprises, as water, water for injections or purified water.

10. The method according to claim 6, wherein the composition comprises, as water, water for injections or purified water.

11. The method according to claim 7, wherein the composition comprises, as water, water for injections or purified water.

12. The method according to claim 8, wherein the composition comprises, as water, water for injections or purified water.

* * * * *